United States Patent [19]

Jessel, Jr. et al.

[11] Patent Number: Plant 5,281

[45] Date of Patent: Sep. 11, 1984

[54] CHRYSANTHEMUM PLANT NAMED MARMALADE

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 420,818

[22] Filed: Sep. 21, 1982

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Marmalade characterized by the combined characteristics of incurved capitulum form; standard capitulum type; light bronze ray floret color; diameter across face of capitulum ranging from 130 to 150 mm. at maturity; uniform nine (9) week photoperiodic flowering response to short days; 55 to 70 cm. plant height when grown single stem with no long days and a low temperature tolerance of 13° C. (55° F.) for initiation and development under controlled short days with a continuous dark period of 12 to 14 hours.

3 Drawing Figures

The present invention comprises a new and distinct cultivar of *Chrysanthemum morifolium,* Ramat., hereinafter referred to by the cultivar name Marmalade. It should be noted that our earlier U.S. Plant Pat. No. 4,122 referred to the same cultivar name. However, the patented plant was never publicly sold or disseminated. Use of the varietal name for the new cultivar is therefore believed proper.

The new cultivar Marmalade is a product of a planned breeding program which had the objective of creating new chrysanthemum cultivars for cut standard mum programs with incurved capitulum form, bronze ray floret color, nine (9) week flowering response, and having the ability to produce commercially acceptable quality in year round programs. Such traits in combination were in need of improvement in previously available commercial cultivars.

Marmalade was originated from a cross made in a controlled breeding program in Barberton, Ohio in 1969. The female parent was Gambit (U.S. Plant Pat. No. 3,481) a bronze, incurved standard originated by the present inventors from a hybridization of two unnamed seedlings. The male parent of Marmalade was Morocco, a yellow incurved standard and disclosed in U.S. Plant Pat. No. 3,191. Morocco was originated from a cross between two unnamed seedlings.

Marmalade was discovered and selected as one flowering plant within the progeny of the stated cross by Walter H. Jessel, Jr. and William E. Duffett on July 7, 1970 in a controlled environment in Barberton, Ohio.

The first act of asexual reproduction of Marmalade was accomplished when vegetative cuttings were taken from the initial selection in October 1970 in a controlled environment in Barberton, Ohio by a technician working under formulations established and supervised by William E. Duffett.

Horticultural examination of selected units initiated June 1978 has demonstrated that the combination of characteristics as herein disclosed for Marmalade are firmly fixed and are retained through successive generations of asexual reproduction.

Marmalade has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Marmalade which in combination distinguish this chrysanthemum as a new and distinct cultivar:

(1) incurved capitulum form;

(2) standard capitulum type;

(3) light bronze ray floret color with moderate color oxidation;

(4) diameter across face of capitulum ranging from 130 to 150 mm. at maturity;

(5) uniform nine (9) week photoperiodic flowering response to short days;

(6) medium plant height (requiring 1 to 2 long day weeks prior to short days to attain a flowered plant height of 80 to 90 cm. for May through October flowerings); and (7) low temperature tolerance of 13° C. (55° F.) for initiation and development when grown in single stem cut standard programs with a continuous dark period of 12 to 14 hours.

The accompanying photographic drawings show typical inflorescence and foliage characteristics of Marmalade, with the colors being as nearly true as possible with illustrations of this type. Sheet 1 is a color photograph of Marmalade grown as a single stem cut standard. Sheet 2 is a black and white photograph showing the top and bottom of leaves of Marmalade at three stages of growth. Sheet 3 is a black and white photograph of three views of the inflorescence of Marmalade.

Of the many commercial cultivars known to the present inventors, the most similar in comparison to Marmalade is Onward, disclosed in U.S. Plant Pat. No. 3,194. Reference is made to attached Chart A which compares certain characteristics of Marmalade to those same characteristics of Onward.

In comparison to Onward, Marmalade has lighter ray floret color, with shorter color retention and a faster rate of oxidation; it has a larger diameter across face of the capitulum by 10 to 15 mm.; it has similar capitulum type, plant height and response to controlled photo periods.

In the following description, color references are made to The Royal Horticultural Society Colour Chart. The color values were determined between 10:30 and 11:00 A.M. on June 30, 1982 under 150 foot-candle light intensity at Salinas, Calif.

CLASSIFICATION

Botanical: *Chrysanthemum morifolium,* Ramat., cv MARMALADE.

Commercial: Cut light bronze standard.

INFLORESCENCE

Capitulum:

*Form.*—Incurved.

*Type.*—Standard.

*Diameter Across Face.*—130 to 150 mm.

Corolla of ray florets:

*Color (general tonality from a distance of three meters).*—Light bronze.

*Color (abaxial).*—Summer (70°-80° F.) 17D to 16C. Winter (55°-65° F.) 14B streaked 25B.

*Color (adaxial).*—Summer (70°-80° F.) 15D. Winter (55°-65° F.) 14B to 14C.

Corolla of disc florets:

*Color (mature).*—6D.

*Color (immature).*—154B.

Reproductive organs:

*Androecium.*—Present disc florets only; scant pollen.

*Gynoecium.*—Present both ray and disc florets.

PLANT

General appearance:

*Height.*—Medium 55 to 70 cm., as a flowering plant from a rooted cutting, with no long days for May through October flowerings and maintaining a minimum nightly 13 hour continuous dark period.

Foliage:

*Color (abaxial).*—147A.

*Color (adaxial).*—147B.

*Shape.*—Deeply lobed and coarsely serrated.

CHART A

COMPARISON OF MARMALADE AND ONWARD

| CULTIVAR | RAY FLORET COLOR | CAPITULUM FORM AND TYPE |
|---|---|---|
| MARMALADE | LIGHT BRONZE | INCURVED STANDARD |
| ONWARD PLANT PAT. NO. 3,194 | BRONZE | SEMI-INCURVED STANDARD |

| CULTIVAR | DIAMETER ACROSS FACE OF CAPITULUM | PLANT HEIGHT | FLOWER RESPONSE PERIOD |
|---|---|---|---|
| MARMALADE | 130 to 150 mm. | MEDIUM 55 to 70 cm. | 9 weeks |
| ONWARD PLANT PAT. NO. 3.194 | 120 to 135 mm. | MEDIUM 55 to 70 cm. | 9 weeks |

COMPARISONS MADE OF PLANTS GROWN AS SINGLE STEM CUT STANDARDS WITH NO LONG DAYS IN SALINAS, CALIFORNIA

We claim:

1. A new and distinct plant of *Chrysanthemum morifolium,* Ramat., known by the cultivar name of Marmalade, as described and illustrated, and particularly characterized as to uniqueness by the combined characteristics of incurved capitulum form; standard capitulum type; light bronze ray floret color; diameter across face of capitulum ranging from 130 to 150 mm. at maturity; uniform nine (9) week flowering response; medium (55 to 70 cm.) height when grown single stem with no long days, and a low temperature tolerance of 13° C. (55° F.) for initiation and development under controlled short days with a continuous dark period of 12 to 14 hours.

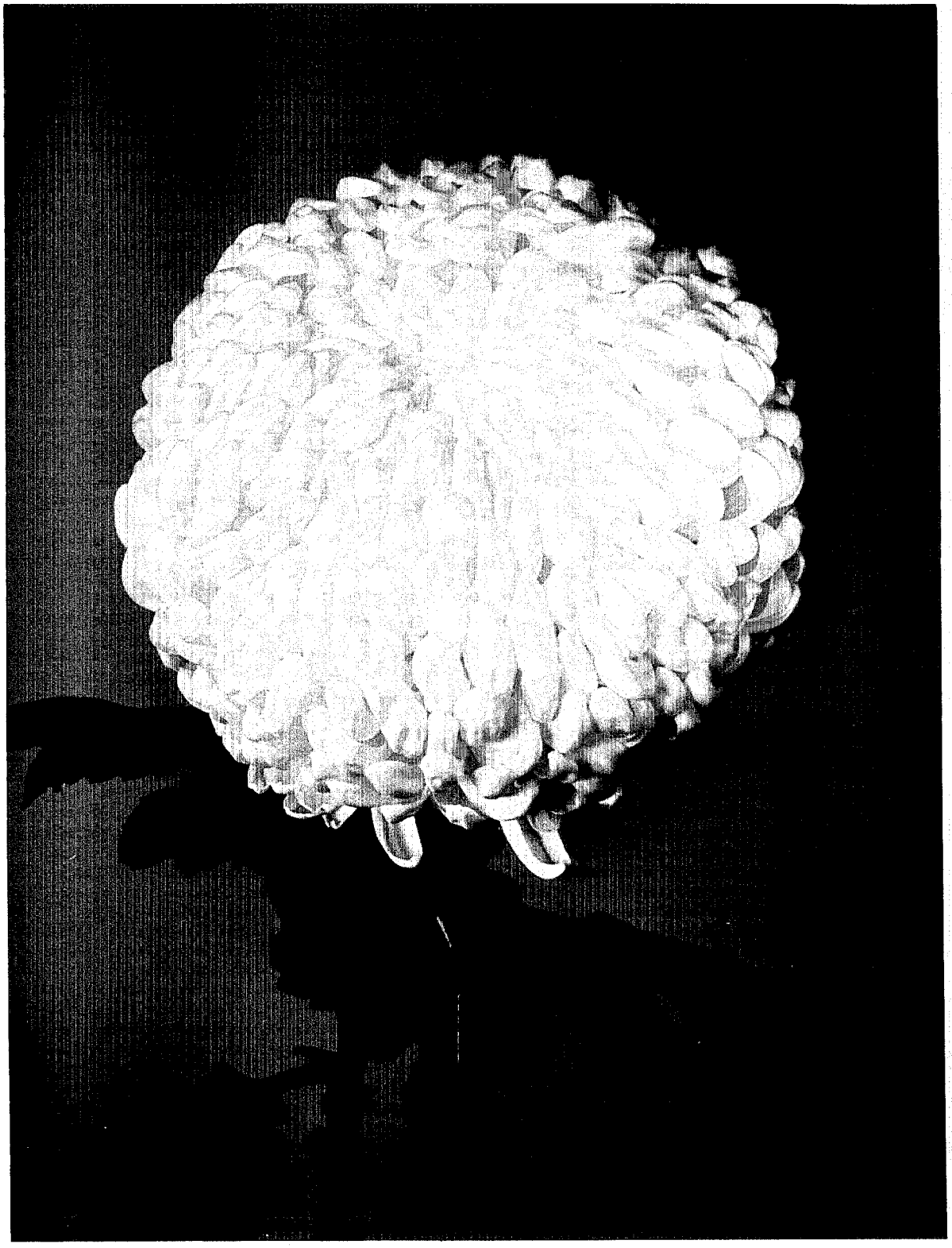

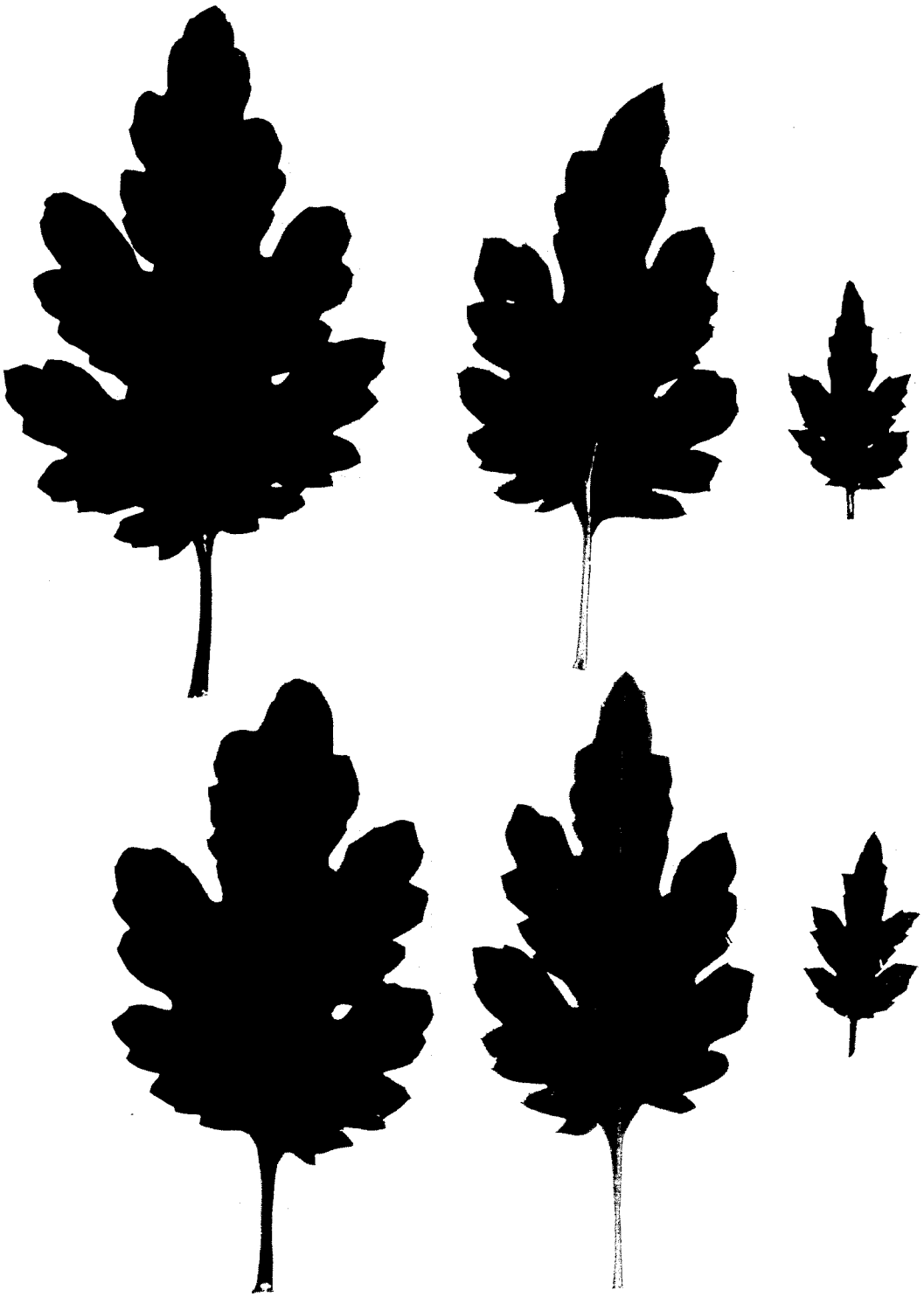

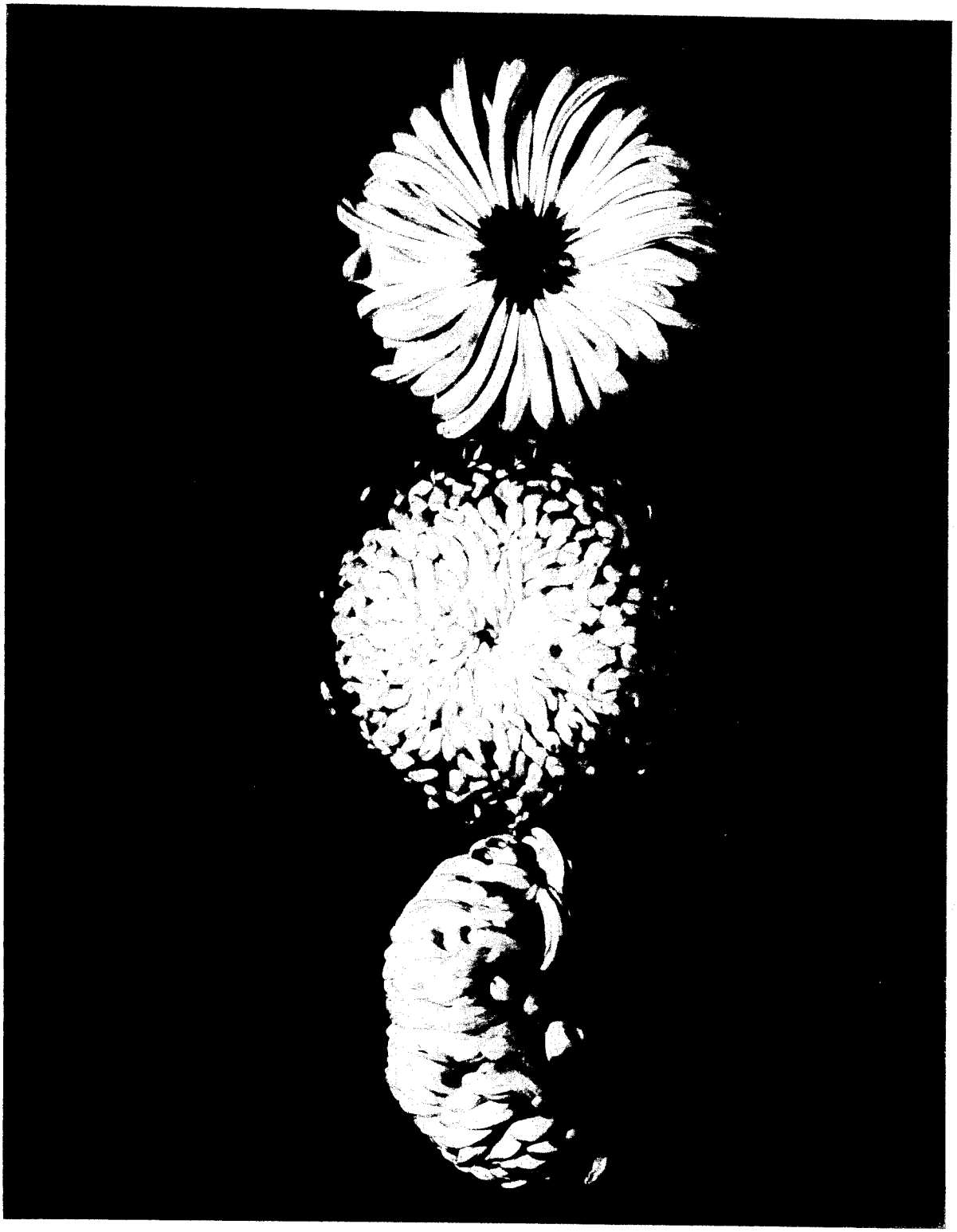

* * * * *